(12) United States Patent
Himuro et al.

(10) Patent No.: US 12,004,924 B2
(45) Date of Patent: Jun. 11, 2024

(54) EARMUFFS

(71) Applicant: JVCKENWOOD Corporation, Yokohama (JP)

(72) Inventors: Toshiyuki Himuro, Yokohama (JP); Hiroshi Uchida, Yokohama (JP)

(73) Assignee: JVCKENWOOD CORPORATION, Yokohama (JP)

( * ) Notice: Subject to any disclaimer, the term of this patent is extended or adjusted under 35 U.S.C. 154(b) by 898 days.

(21) Appl. No.: 17/030,719

(22) Filed: Sep. 24, 2020

(65) Prior Publication Data

US 2021/0100689 A1    Apr. 8, 2021

(30) Foreign Application Priority Data

Oct. 8, 2019   (JP) .................. 2019-184902

(51) Int. Cl.
*A61F 11/14*        (2006.01)
*H04R 1/10*         (2006.01)

(52) U.S. Cl.
CPC ............... *A61F 11/14* (2013.01); *H04R 1/10* (2013.01); *H04R 2201/10* (2013.01)

(58) Field of Classification Search
CPC ........ A61F 11/14; H04R 1/10; H04R 2201/10
See application file for complete search history.

(56) References Cited

U.S. PATENT DOCUMENTS

| | | | | |
|---|---|---|---|---|
| 4,572,323 A * | 2/1986 | Randall | ................... | A61F 11/14 381/372 |
| 4,830,138 A * | 5/1989 | Palmaer | ................... | A61F 11/14 381/372 |
| 5,241,971 A * | 9/1993 | Lundin | ................... | A42B 3/166 381/372 |
| 5,920,911 A * | 7/1999 | Cushman | ................ | A61F 11/14 181/129 |
| 5,996,123 A * | 12/1999 | Leight | ..................... | A61F 11/14 181/129 |
| 9,980,855 B2 * | 5/2018 | Hansson | .................. | A61F 11/14 |
| 10,792,190 B2 * | 10/2020 | Håkansson | .......... | H04R 1/1058 |

FOREIGN PATENT DOCUMENTS

| | | |
|---|---|---|
| JP | 2008-520337 A | 6/2008 |
| SE | 0484306 A1 * | 5/1992 |

* cited by examiner

*Primary Examiner* — Forrest M Phillips
(74) *Attorney, Agent, or Firm* — Nath, Goldberg & Meyer; Jerald L. Meyer (57) ABSTRACT

Earmuffs include a bowl-shaped housing base having a first engagement portion, an annular plate-shaped base plate having a second engagement portion on one side and a third engagement portion on the other side, and is integrated with the housing base by causing the second engagement portion to be engaged with the first engagement portion, and a pad portion that includes a pad fixed on one side and a pad base having a fourth engagement portion on the other side, and is integrated with the base plate by causing the fourth engagement portion to be engaged with the third engagement portion. The base plate has a groove portion adjacent to the third engagement portion and the pad base has a rib that enters the groove portion. The rib enters the groove portion and restricts an inclination of the third engagement portion involved with an engagement with the fourth engagement portion.

5 Claims, 10 Drawing Sheets

EARMUFFS

CROSS REFERENCE TO RELATED APPLICATION

This application is based upon and claims the benefit of priority under 35 U.S.C. § 119 from Japanese Patent Application No. 2019-184902, filed on Oct. 8, 2019, the entire contents of which are incorporated herein by reference.

BACKGROUND

The present invention relates to earmuffs.

Japanese Patent Application Publication No. 2008-520337 discloses earmuffs including a pair of main bodies to be fitted to the left and right ears and a headband connected to the pair of main bodies. Each of the main bodies of the earmuffs disclosed in the above document includes a cup-shaped cap formed with an air chamber at an inside and a ring-shaped element that is fixed with a sealing ring to be contacted with a side of a head and is attached to an opening portion of the cap. The cap and the ring-shaped element are integrated by causing a pair of engagement members with snap lock structures to be engaged with each other across pressure equalizing means. The pressure equalizing means is assumed to be a ring-shaped member having flexibility.

SUMMARY

In the earmuffs disclosed in the above document, adverse influences caused by variations in dimensions of the cap and the ring-shaped element are eliminated or reduced by interposing the pressure equalizing means between the engagement members, and thus, it is assumed that the earmuffs have a consistent muffling capability between individual different 1 products in terms of the sound isolation performance.

However, if variations in the thickness of the pressure equalizing means are also taken into consideration, in a case where the pressure equalizing means is thick, a possibility of an occurrence of a gap between the engagement members may not be eliminated depending on the variations in the dimension of the engagement member, and in terms of product manufacturing, it has been possible that a high sound isolation performance may not be obtained stably.

An aspect of one or more embodiments provides earmuffs include a bowl-shaped housing base that includes a first engagement portion on one side thereof, an annular plate-shaped base plate that includes a second engagement portion and a third engagement portion respectively on a first surface and a second surface on a side opposite to the first surface, and is integrated with the housing base by causing the second engagement portion to be engaged with the first engagement portion; and a pad portion that includes a pad fixed on the one side and a pad base including a fourth engagement portion on the other side opposite to the one side, and is integrated with the base plate by causing the fourth engagement portion to be engaged with the third engagement portion; and in the earmuffs, the base plate includes a groove portion adjacent to the third engagement portion and the pad base includes a rib that enters the groove portion; and the rib enters the groove portion and restricts an inclination of the third engagement portion involved with an engagement with the fourth engagement portion in a state where the pad base is integrated with the base plate by causing the fourth engagement portion to be engaged with the third engagement portion.

DETAILED DESCRIPTION

Earmuffs according to an embodiment of the present invention will be described by referring to earmuffs 91 of an example and earmuffs 91A and earmuffs 91B of a modified example 1 and a modified example 2 respectively. In the following descriptions, a state in which the earmuffs 91 are worn to a head H of a user is simply referred to as a worn state.

EXAMPLE

Figure 1:
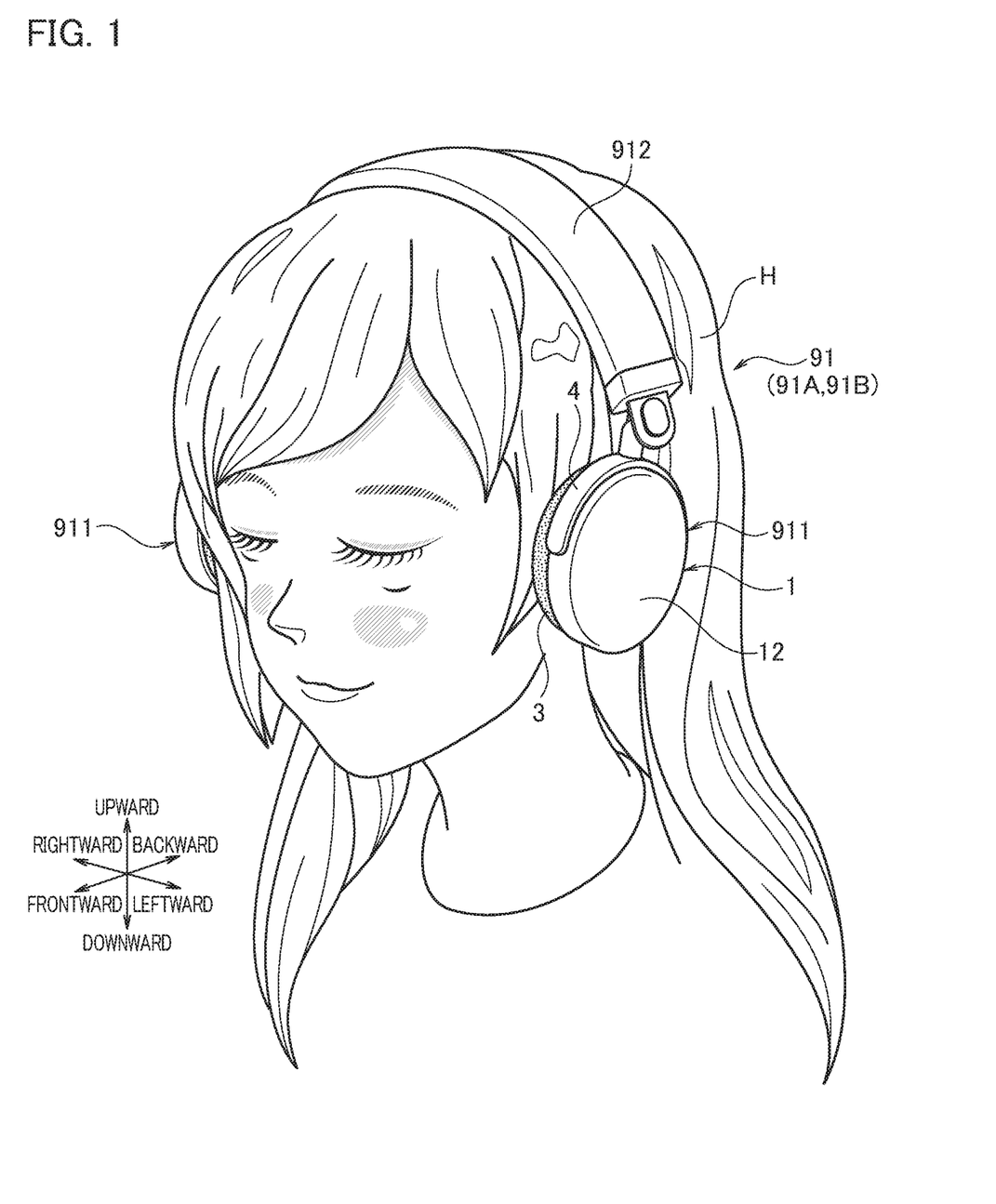
FIG. 1 is a diagram illustrating a state in which earmuffs 91 that are an example of earmuffs according to an embodiment of the present invention is worn on a head H.

A schematic structure of the earmuffs 91 will be described. FIG. 1 is a perspective view illustrating a state in which the earmuffs 91 are worn to the head H of the user. For explanatory convenience, each of the upward, downward, leftward, rightward, frontward, and backward directions is defined as each of the directions indicated by arrows in FIG. 1.

The earmuffs 91 include a pair of main bodies 911 that are fitted so as to cover the entire left and right auricles, and a headband 912 that is connected to the pair of main bodies 911 and is stretched over a top of the head or the like. Types of the earmuffs 91 are categorized into a so-called over-the-ear type.

Figure 2:
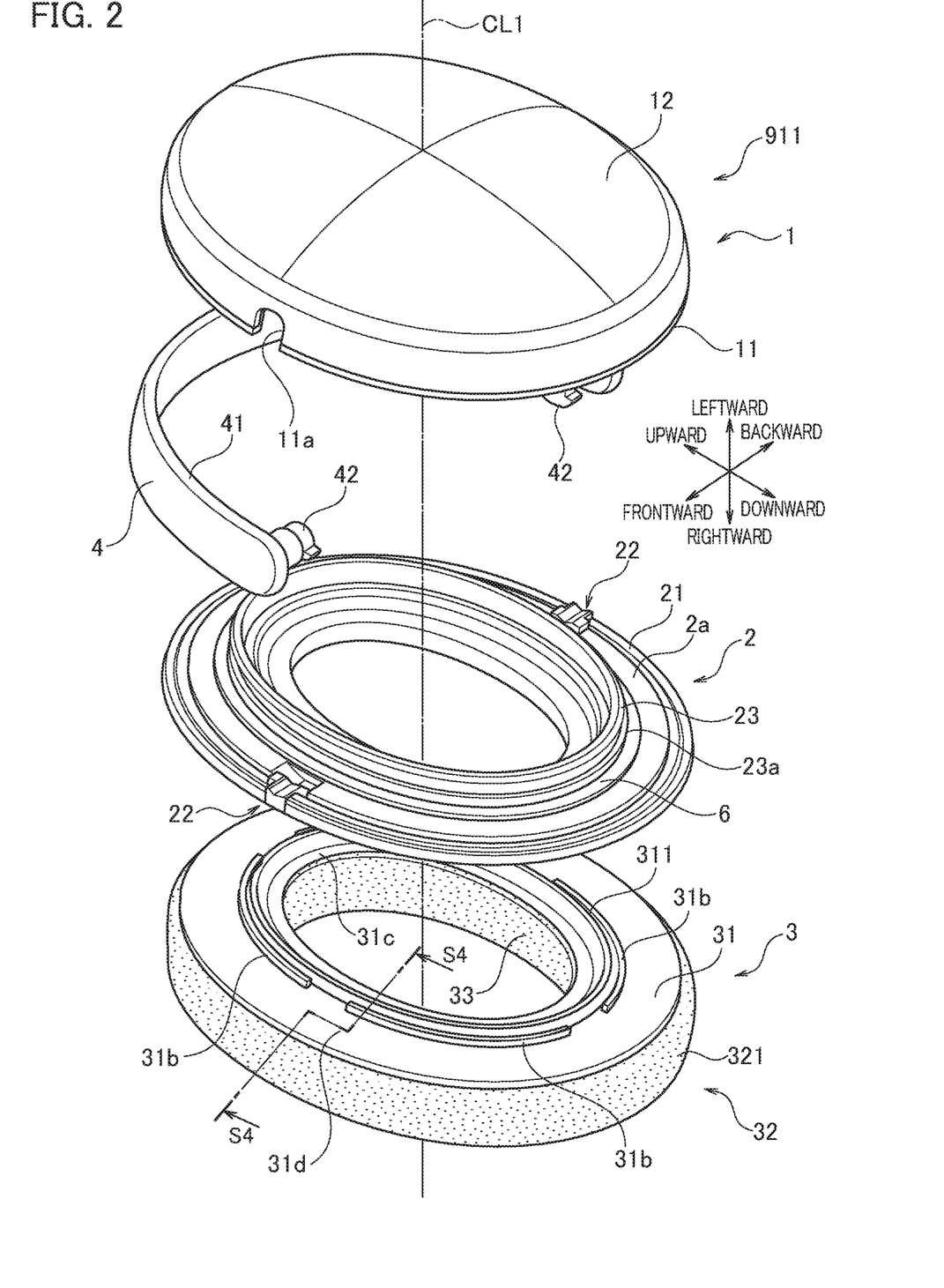
FIG. 2 is an exploded view illustrating a main body 911 of an earmuff 91.
Figure 3:
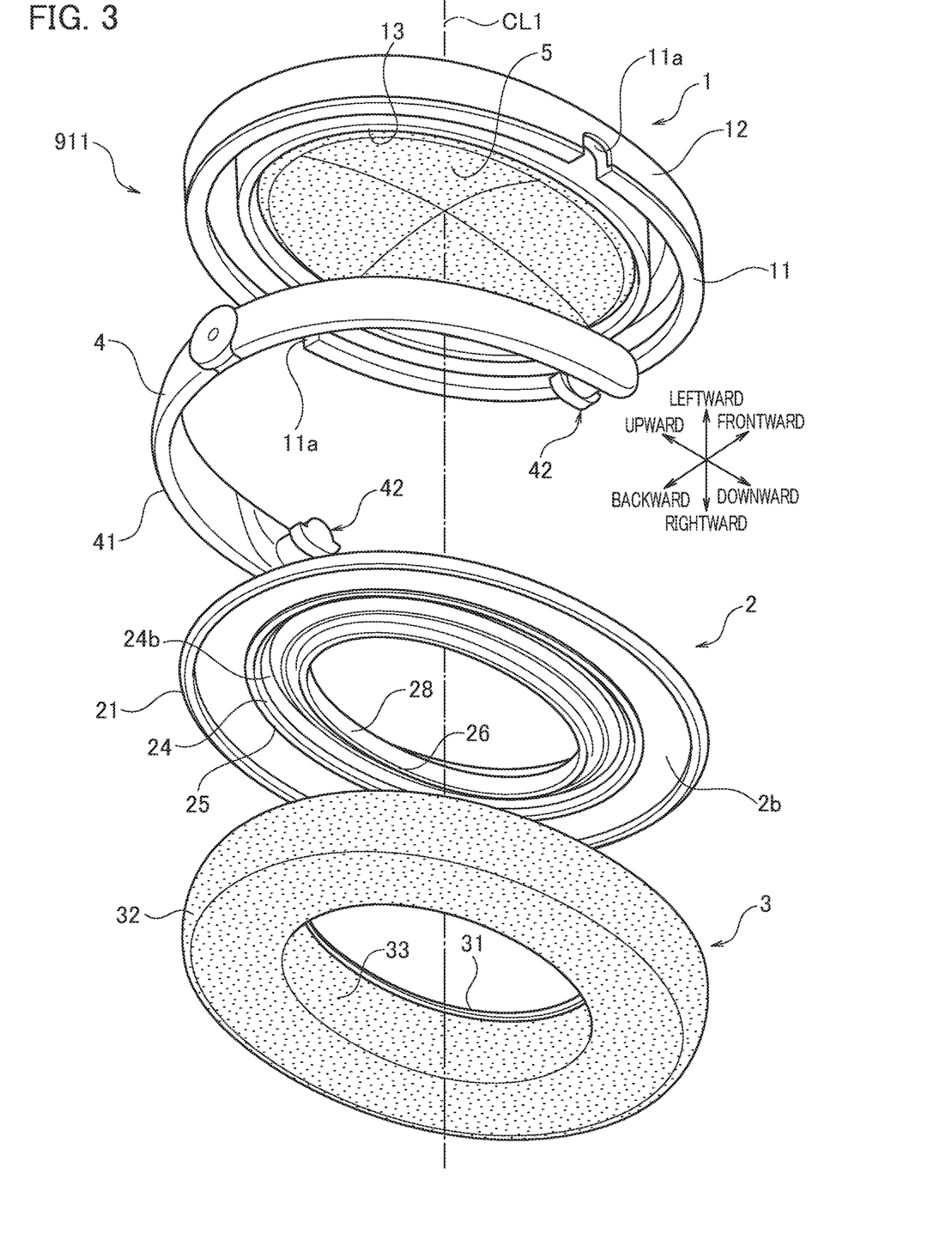
FIG. 3 is an exploded view of a main body 911 when the main body 911 is viewed from a direction opposite to the viewing direction in FIG. 2.

FIG. 2 is an exploded perspective view when a main body 911 of the pair of main bodies 911 fitted to a left ear is viewed from a left front obliquely below direction, and FIG. 3 is an exploded perspective view when the main body 911 fitted to the left ear is viewed from a right front obliquely above direction.

As illustrated in FIG. 2 and FIG. 3, the main body 911 includes a housing portion 1, a base portion 2, a pad portion 3, and a hanger portion 4. The housing portion 1 is formed to have a bowl shape such that one side that is the head H side is opened when the earmuffs are in the worn state. The base portion 2 is a resin member formed to have an annular plate shape and is attached to the housing portion 1 by a snap-fit structure. The base portion 2 is arranged between the housing portion 1 and the pad portion 3 for connecting the both members. The pad portion 3 has a ring shape and is manually attached to the base portion 2 by a human hand in a detachable manner by the snap-fit structure. The pad portion 3 is a member in contact with a side of the head when the earmuffs are the worn state and a portion in contact with the side of the head is formed by using a soft material to enhance the adhesiveness and the sealability with the side of the head. The hanger portion 4 is connected to the housing portion 1 in a manner rockable about an axis line that becomes substantially horizontal when the earmuffs are in the worn state.

Figure 4:
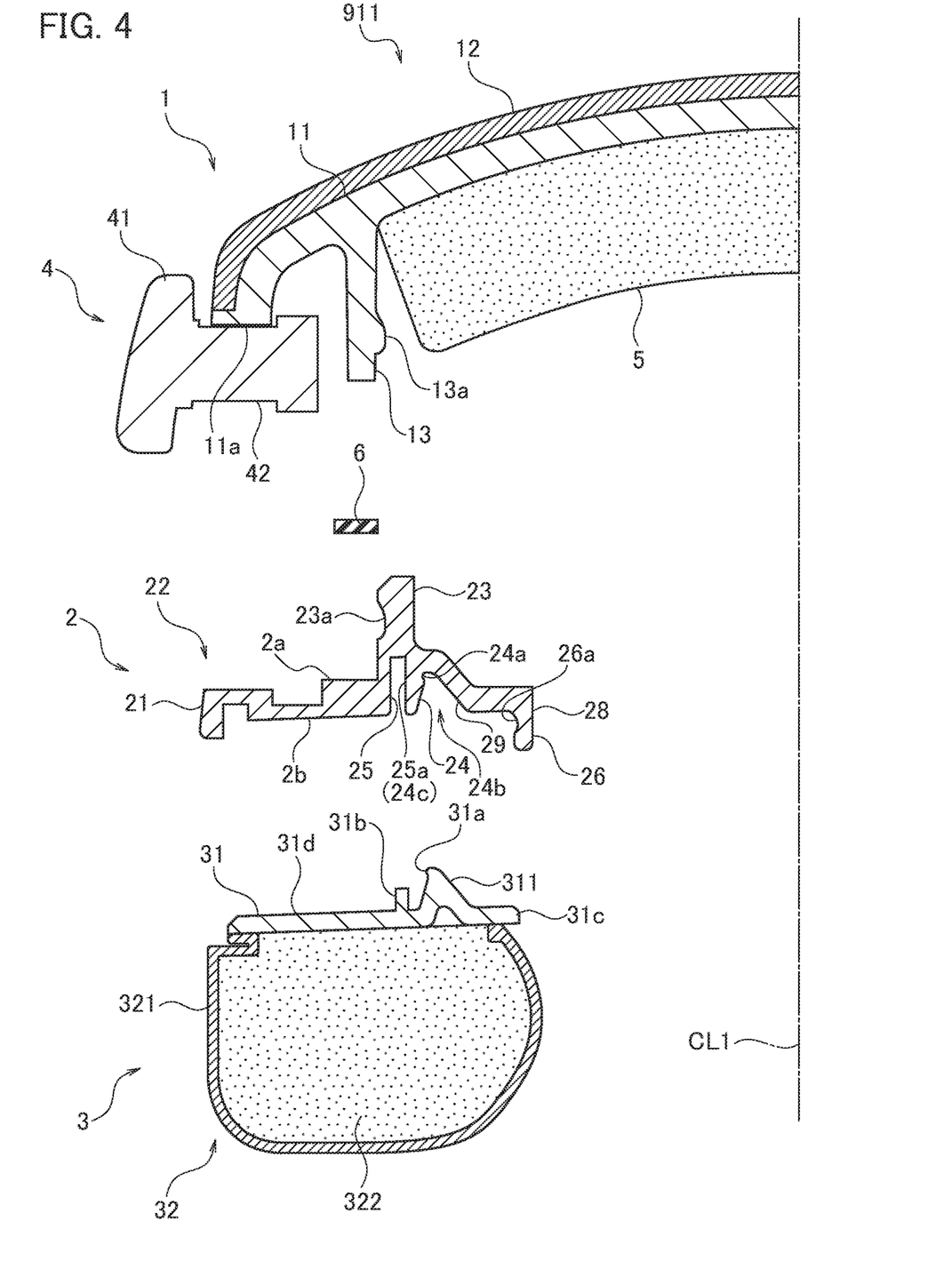
FIG. 4 is a partial cross-sectional, exploded view of a main body 911.
Figure 5:
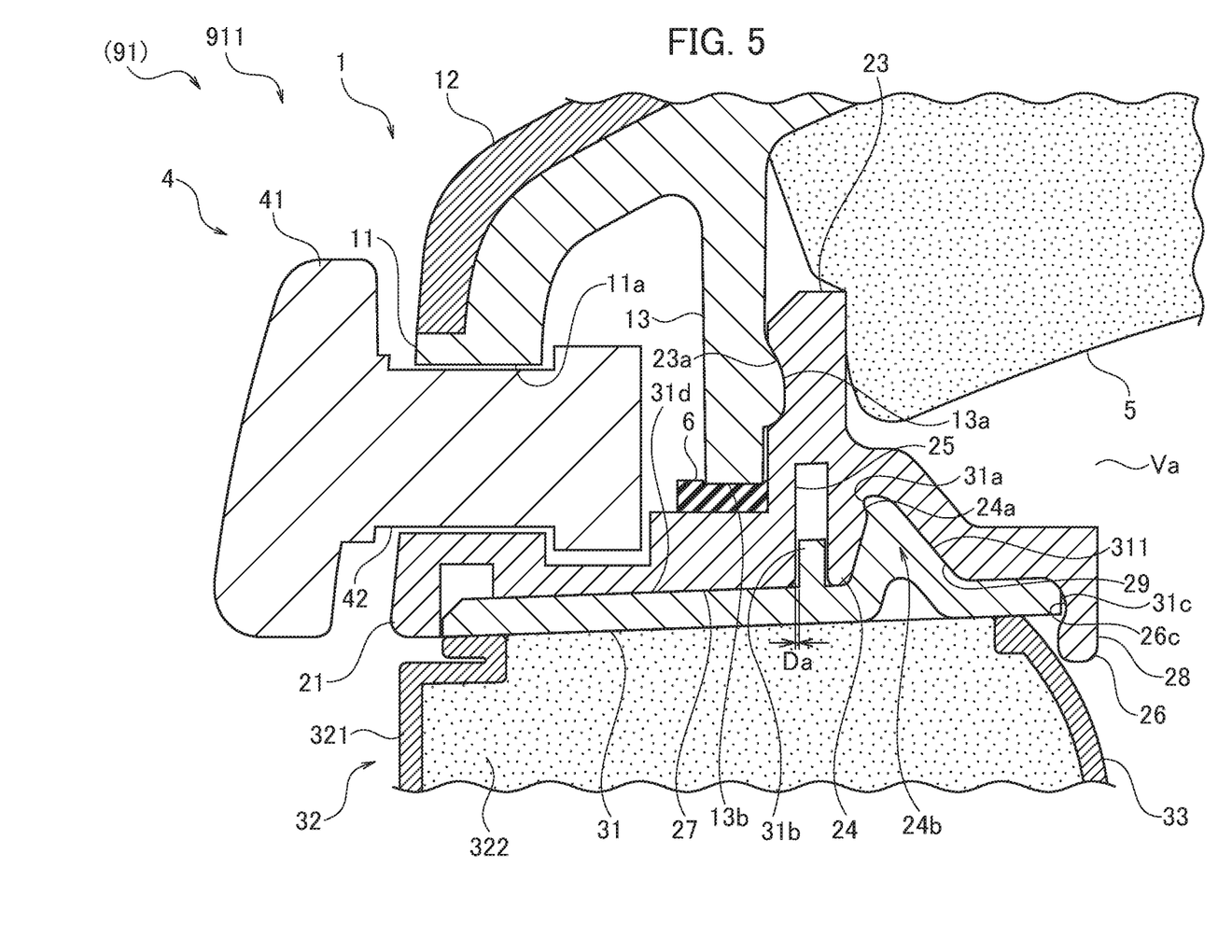
FIG. 5 is a partial cross-sectional view of a main body 911.

Next, with reference to FIG. 2 to FIG. 5, a detailed structure of the main body 911 will be described. FIG. 4 is a partial cross-sectional, exploded view at a S4-S4 position in FIG. 2. FIG. 5 is a partial cross-sectional view at the S4-S4 position in FIG. 2 in a state where the main bodies 911 are assembled.

The housing portion 1 is formed to have a vertically long oval shape when the earmuffs are in the worn state. The housing portion 1 has a two-layer structure of inner and outer layers and has a housing base 11 at an inward side that is formed by the injection molding of a resin and a cover 12 that is covered on an outside of the housing base 11. Example resins of the housing base 11 include ABS (acrylonitrile butadiene styrene). The cover 12 is formed of thermal plastic elastomer, aluminum or the like, and is a member that becomes an accent of an appearance design.

The housing portion 1 has a notch portion 11a at a middle position in a vertical direction of a front edge and a rear edge when the earmuffs are in the worn state. An engagement wall portion 13 that is a first engagement portion having a shape substantially similar to an external shape of the housing base 1 stands on an inner surface of the housing base 11. Further, a sound absorption member 5 is arranged at a portion surrounded by the engagement wall portion 13 on the inner surface of the housing base 11. As illustrated in FIG. 4 and FIG. 5, provided to an inner circumference surface of the engagement wall portion 13 is an engagement convex portion 13a that extends in a peripheral direction and protrudes inwardly.

The base portion 2 includes an annular plate-shaped base plate 21 that is formed by the injection molding of a resin, has an oval external shape in accordance with the external shape of the housing portion 1 and has an oval-shaped opening portion 28 at the center thereof. Resin examples include ABS. The base plate 21 has hanger supporting portions 22 that are respectively positioned at segments of an outer surface 2a (a first surface) on a side further distal than the head H, the segments positions corresponding to a pair of notch portions 11a of the housing portion 1. Standing on the outer surface 2a over an entire circumference is an engagement rib portion 23 that is a second engagement portion fitting along an inward side of the engagement wall portion 13 of the housing portion 1 when the housing portion 1 and the based portion 2 are combined as illustrated in FIG. 5. The engagement rib portion 23 is formed with an engagement concave portion 23a to be engaged with the engagement convex portion 13a of the engagement wall portion 13 over an entire circumference.

In the base plate 21, a peripheral groove portion 25 is formed to a portion of an inner surface 2b (a second surface) on an inward side (the head H side), the position corresponding to a position of the engagement rib portion 23 when the earmuffs are in the worn state. The peripheral groove portion 25 is formed to face outward and to be hollowed when the earmuffs are in the worn state. The peripheral groove portion 25 is provided to the portion of the inner surface 2b corresponding to the position of the engagement rib portion 23 as a so-called lightening portion for preventing the occurrence of sink marks caused by the injection molding.

Here, as illustrated in FIG. 2, a center line of the main body 911 is set as a center line CL1 that passes through the center of an oval external shape of the housing portion 1 and is perpendicular to the base plate 21. As illustrated in FIG. 4 and FIG. 5, an inner wall surface 25a that is one inner surface on the center line CL1 side of the peripheral groove portion 25 is an outer wall surface 24c of a peripheral wall portion 24 as a third engagement portion that is a peripheral rib having flexibility in a direction separating from or contacting with the center line CL1.

The peripheral wall portion 24 has, on a bottom side thereof, as a concave portion, a peripheral wall concave portion 24a that extends in a peripheral direction and is hollowed toward a side opposite to the center line CL1. An inclined surface 29 that faces the peripheral wall portion 24 is provided on the center line CL1 side of the peripheral wall portion 24, and a peripheral concave portion 24b having a substantially triangle-shaped cross-section is formed between the peripheral wall portion 24 and the inclined surface 29. The peripheral concave portion 24b is formed along the peripheral wall portion 24 over an entire circumference.

An inner edge wall portion 26 that extends on the pad portion 3 side along the center line CL1 is formed to an inner edge portion of the annular plate-shaped base plate 21 over an entire circumference. A concave portion 26a that is hollowed toward the center line CL is formed on an outer peripheral surface on a side opposite to the center line CL1 of the inner edge wall portion 26 over an entire circumference.

As illustrated in FIG. 2 and FIG. 3, the hanger portion 4 has an arm 41 formed to have an arc shape along an external shape of the housing base 11 and engagement portions 42 formed to protrude inward respectively at both ends of the arm 41. A middle portion of the arm 41 is connected to a member on the housing side. As illustrated in FIG. 4 and FIG. 5, the engagement portions 42 is sandwiched between the notch portion 11a of the housing portion 1 and the hanger supporting portion 22 of the base portion 2, and is held such that a rotational movement with a predetermined angle is allowed.

As illustrated in FIG. 2 and FIG. 4, the pad portion 3 has a pad base 31 formed to have an annular plate shape by the injection molding of a resin and a pad 32 that is fixed to a surface on an inward side (on a right side) of the pad base 31 when the earmuffs are in the worn state. The pad 32 is formed by covering a cushion 322 that is a soft member such as a sponge with a skin portion 321 made of artificial leather.

As illustrated in FIG. 2 and FIG. 5, a peripheral convex portion 311 that is a protruding fourth engagement portion with a triangle-shaped cross-section is formed on a surface on an outward side (on a left side) of the pad base 31 when the earmuffs are in the worn state. An engagement convex portion 31a that protrudes in a direction away from the center line CL1 is formed on the outer peripheral side of a tip portion of the peripheral convex portion 311 over an entire circumference. Formed to the pad base 31 is a rib 31b that is adjacent to the outer peripheral side of the peripheral convex portion 311. The rib 31b extends in the peripheral direction and protrudes at a right angle to the pad base 31.

As illustrated in FIG. 2 and FIG. 4, a ring 6 is an oval-shaped ring member that can be fitted to the bottom on the outer peripheral side of the engagement rib portion 23 in the base plate 21. The ring 6 is elastic at least in a compression direction. The ring 6 without the air permeability or with small air permeability is preferable and material examples of the ring 6 include a silicone rubber.

The above described housing portion 1, base portion 2, ring 6, and pad portion 3 can be assembled as illustrated in FIG. 5. Specifically, the ring 6 is fitted to the bottom on the outer peripheral side of the engagement rib portion 23 in the base plate 21. Next, the base portion 2 is integrated with the housing portion 1 by causing the engagement convex portion 13a of the engagement wall portion 13 of the housing portion 1 to be engaged with the engagement concave portion 23a of the engagement rib portion 23 in the base plate 21 as the snap-fit. In this state, a tip portion 13b of the engagement wall portion 13 of the housing base 11 pushes and compresses the ring 6.

Next, the pad portion 3 is integrated with the base plate 21 by causing the peripheral convex portion 311 of the pad base 31 to be entered into the peripheral concave portion 24b of the base plate 21 and causing the engagement convex portion 31a of the peripheral convex portion 311 to be engaged with the peripheral wall concave portion 24a of the peripheral wall portion 24 in the base plate 21 as the snap-fit. In this state, an inner edge portion 31c of the pad base 31 is engaged with the concave portion 26a in the inner edge wall portion 26 of the base plate 21. Further, during the entry of the peripheral convex portion 311 to the peripheral concave portion 24b, the rib 31b of the pad base 31 enters the peripheral groove portion 25 that is a lightening portion of the base plate 21. The peripheral groove portion 25 is formed on a side where the peripheral wall portion 24 is deflected and inclined by being involved in the engagement with the peripheral convex portion 311, and the rib 31b is in contact with or is in proximity to the outer wall surface 24c of the peripheral wall portion 24 to restrict an inclination of the peripheral wall portion 24 on the outer peripheral side. That is, the rib 31b enters the peripheral groove portion 25 by sliding or being in proximity to the inner wall surface 25a of the peripheral groove portion 25. Further, a predetermined gap Da is formed between a facing inner wall surface 25b that faces the inner wall surface 25a of the peripheral groove portion 25 and the rib 31b. This enables the base plate 21 to be deformed such that the facing inner wall surface 25b of the peripheral groove portion 25 is in proximity to the inner wall surface 25a and a groove width becomes narrow.

By the rib 31b entering the peripheral groove portion 25 and restricting the inclination of the peripheral wall portion 24 on the outer peripheral side, the engagement between the peripheral wall portion 24 and the inclined surface 29 in the base plate 21 and the peripheral convex portion 311 in the pad base 31 entering the peripheral concave portion 24b becomes more tight, and a degree of adhesion between the base plate 21 and the pad base 31 is improved. Therefore, a sound trying to enter, from an outside, to an air chamber Va that is an internal space of the earmuffs 91 after passing between the base plate 21 and the pad base 31 is well isolated, and according to the earmuffs 91, a high sound isolation performance can be obtained. Further, by the rib 31b preventing the inclination of the peripheral wall portion 24, adverse influences of variations in dimensions of the base plate 21 and the pad base 31 to the degree of adhesion between the base plate 21 and the pad base 31 can be more suppressed than when the rib 31b is absent. This enablers the stable obtaining of the high sound isolation performance for the earmuffs 91.

On the other hand, a ring-shaped ring 6 in a compressed state is interposed between the base plate 21 and the housing base 11 over an entire circumference, and the degree of adhesion between the base plate 21 and the housing base 11 is improved. Therefore, a sound trying to enter, from an outside, to the air chamber Va that is an internal space of the earmuffs 91 after passing between the base plate 21 and the housing base 11 is well isolated, and according to the earmuffs 91, a high sound isolation performance can be obtained.

Further, by an elastic repulsive power of the compressed ring 6, a pad face portion 27 that is a face on the pad base 31 side of the base plate 21 biases a pad face portion 31d that is a face on the base plate 21 side of the pad base 31. This further improves the degree of adhesion between the pad face portion 27 and the pad face portion 31d regardless of the variation in dimension of the base plate 21 and the pad base 31. Further, this enables the stable obtaining of the higher sound isolation performance for the earmuffs 91.

Further, while the degree of adhesion between the pad face portion 27 and the pad face portion 31d is improved by the elastic repulsive power of the ring 6, it is possible that a segment of the base plate 21 in the vicinity of the ring 6 is deformed. Further, if a deformation range of the base plate 21 is accidentally expanded, it is possible that the degree of adhesion between the peripheral concave portion 24b and the peripheral convex portion 311 engaged with the peripheral concave portion 24b is affected.

However, in the housing portion 1 of the earmuffs 91, the ring 6 is provided in a prescribed manner at a position in the vicinity of the peripheral groove portion 25 and on a side opposite to the peripheral wall portion 24 across the peripheral groove portion 25. Therefore, even if the base plate 21 is deformed due to the elastic repulsive power of the ring 6 compressed in the thickness direction, the deformation is absorbed by the expansion/contraction deformation of a gap of the peripheral groove portion 25 and is not propagated to the peripheral wall portion 24. Therefore, the deformation of the base plate 21 caused by the elastic repulsive power of the ring 6 hardly affects the degree of adhesion between the peripheral concave portion 24b and the peripheral convex portion 311 engaged with the peripheral concave portion 24b. This enables stable and certain obtaining of the high sound isolation performance for the earmuffs 91.

As described above, it is sufficient if the earmuffs 91 include either one of the ring 6 provided in a prescribed manner in the vicinity of the peripheral groove portion 25 on either one side of inward and outward sides of the peripheral groove portion 25 in association with the peripheral groove portion 25 formed on the base plate 21 as a lightening portion and the rib 31b that enters the peripheral groove portion 25 and prevents or suppresses the radial and outward inclination of the peripheral wall portion 24 involved with the engagement with the pad base 31. In either case, an effect of being able to stably obtain the high sound isolation performance for the earmuffs 91 is achieved.

Figure 8:
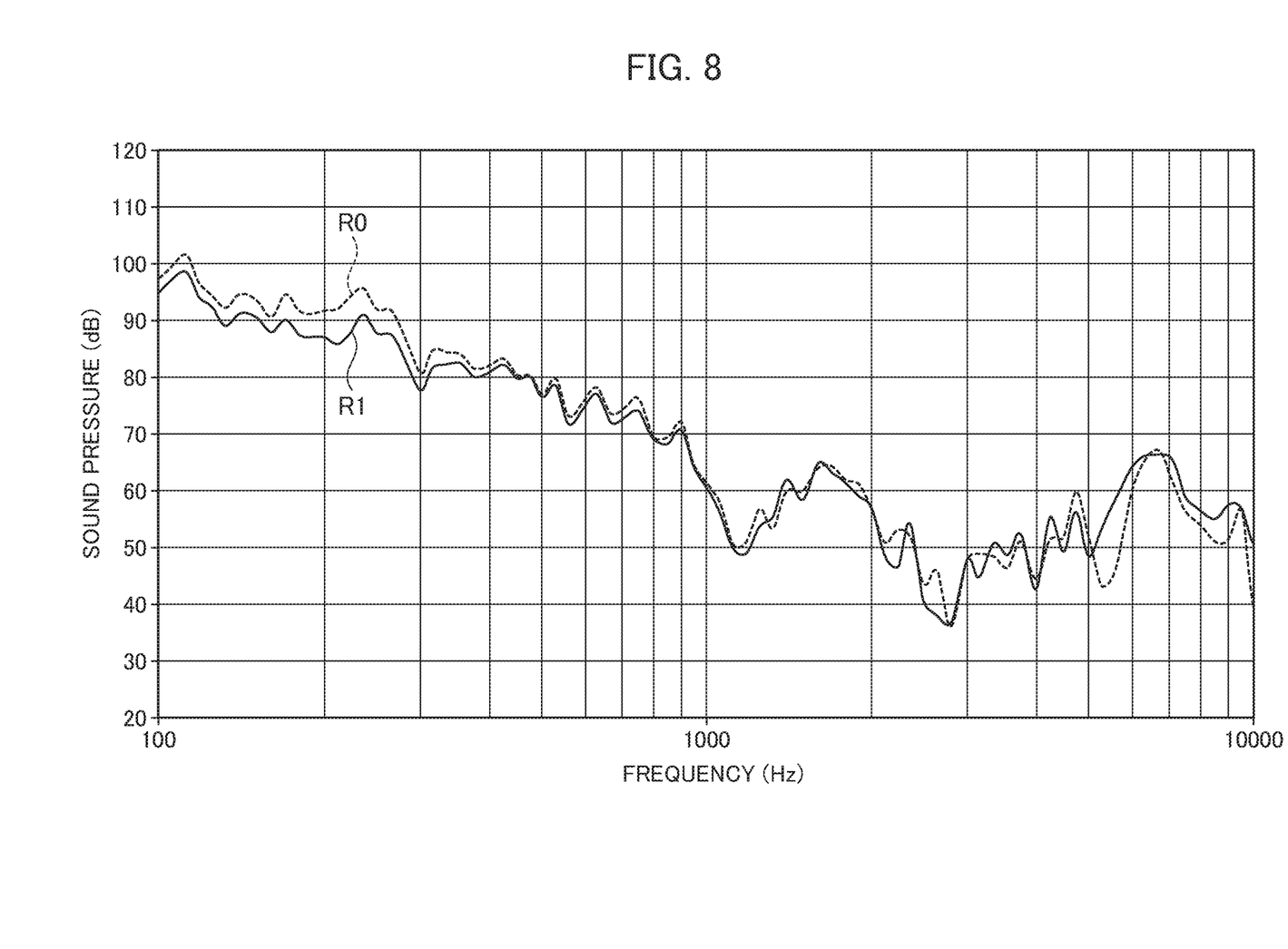
FIG. 8 is a graph for explaining a sound isolation performance of earmuffs 91A having a main body 911A.
Figure 9:
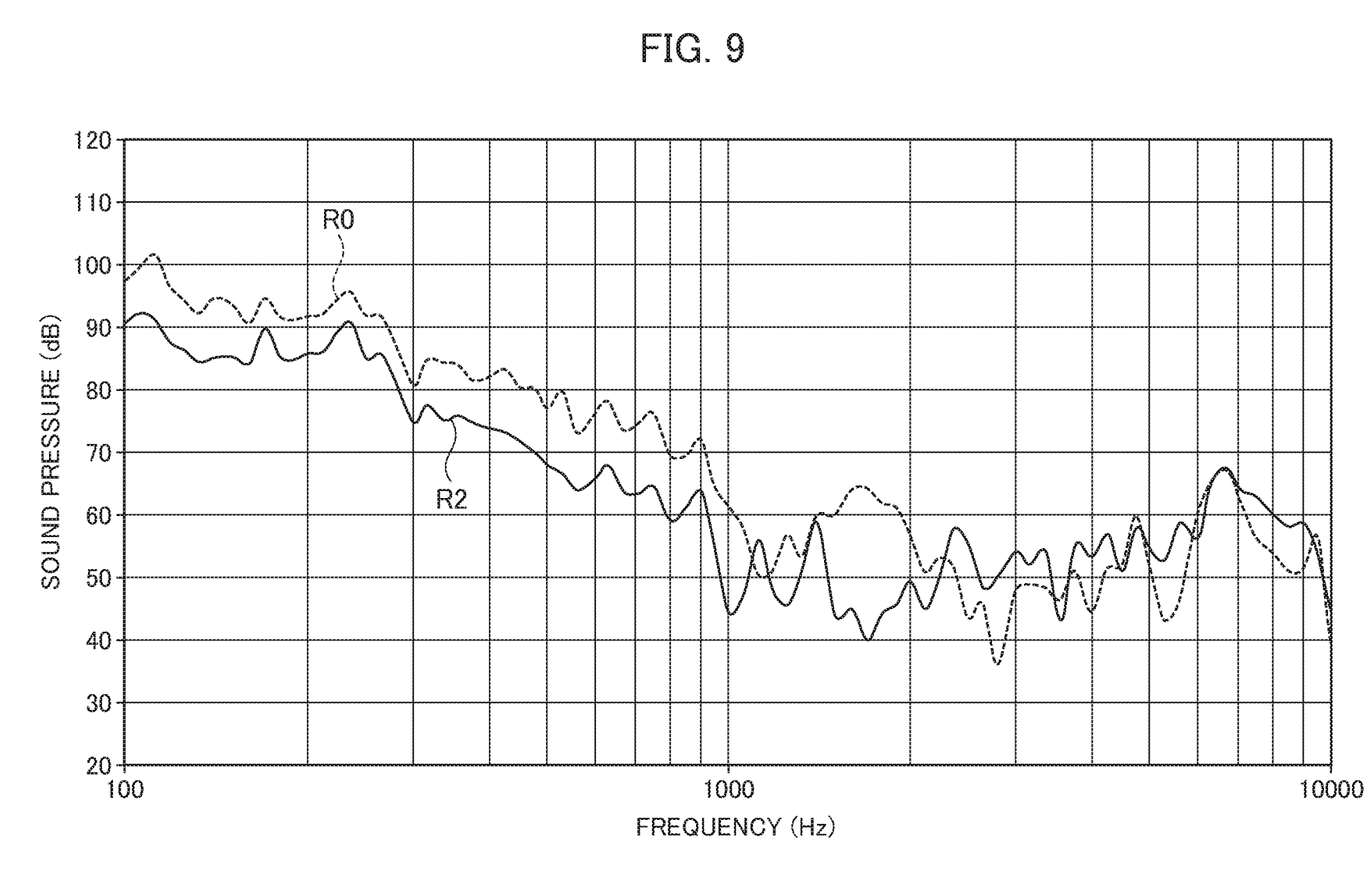
FIG. 9 is a graph for explaining a sound isolation performance of earmuffs 91B having a main body 911B.
Figure 10:
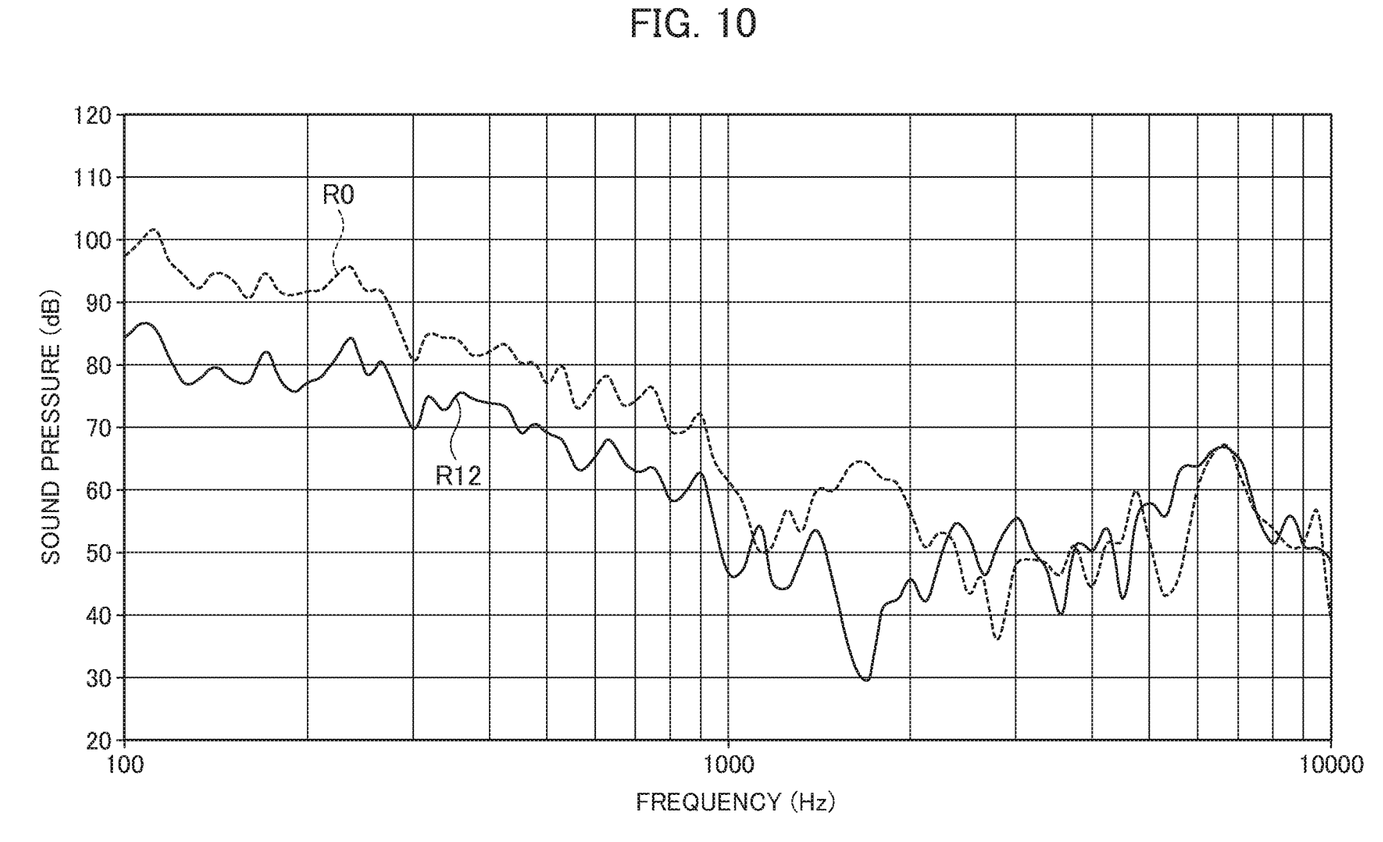
FIG. 10 is a graph for explaining a sound isolation performance of earmuffs 91 having a main body 911.

FIG. 8 to FIG. 10 are graphs showing frequency characteristics measured for evaluating the sound isolation performance of the earmuffs 91. The frequency characteristics shown in these graphs were measured based on the following method. That is, first, in the method, the earmuffs 91 were worn on a dummy head. The dummy is obtained by mounting a microphone on a pore corresponding to an ear canal. Next, in the method, a sweep sound of a predetermined magnitude in a sound range from at least 100 Hz to 10000 Hz was generated at an outside in a state where the earmuffs 91 were worn, then, the sweep sound was collected by the microphone of the dummy, and the frequency characteristic was measured. FIG. 8 to FIG. 10 illustrate, with short dashed lines, a frequency characteristic R0 of a comparative example of earmuffs of not having both the rib 31b and the ring 6.

Figure 6:
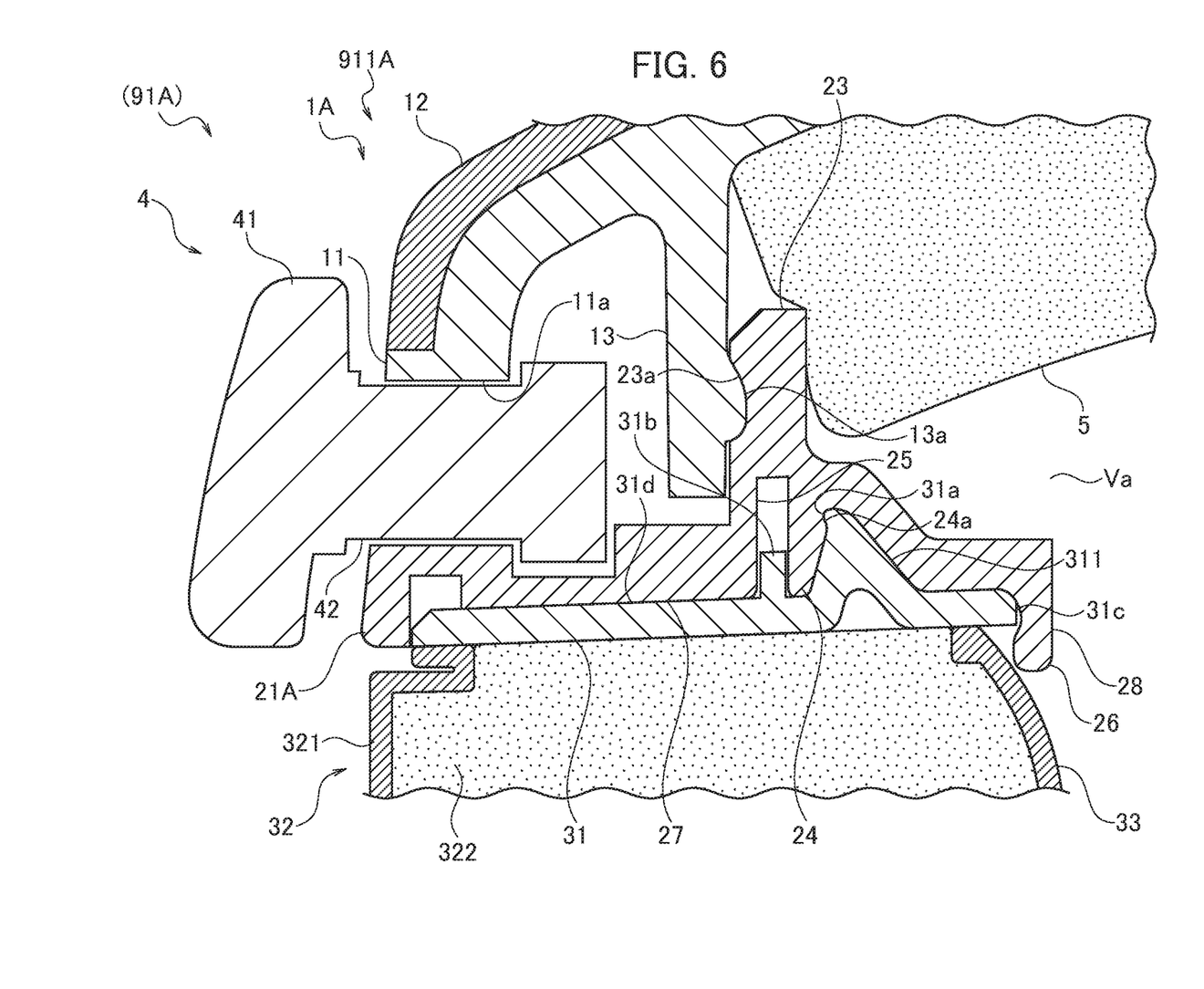
FIG. 6 is a partial cross-sectional view of a main body 911A that is a modified example 1 of a main body 911.
Figure 7:
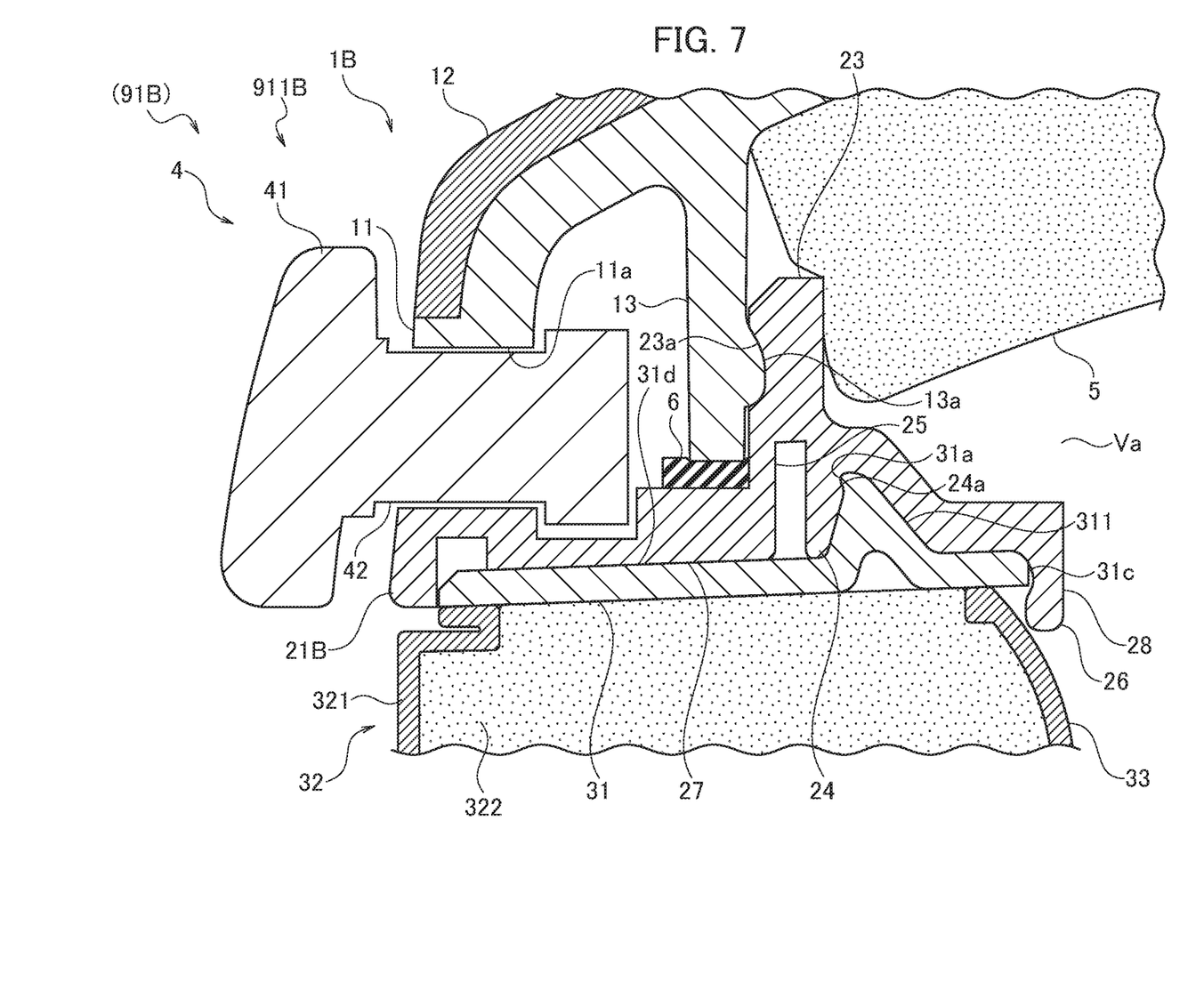
FIG. 7 is a partial cross-sectional view of a main body 911B that is a modified example 2 of a main body 911.

With respect to the earmuffs 91, as illustrated in FIG. 6, by defining a main body only having the rib 31b from between the rib 31b and the ring 6 as a main body 911A, earmuffs having the main body 911A are defined as earmuffs 91A and as illustrated in FIG. 7, by defining a main body only having the ring 6 as a main body 911B, earmuffs having the main body 911B are defined as earmuffs 91B.

FIG. 8 is a graph showing the frequency characteristic R0 (a short dashed line) and a frequency characteristic R1 of the earmuffs 91A only having the rib 31b (a solid line). FIG. 9 is a graph showing the frequency characteristic R0 (the short dashed line) and a frequency characteristic R2 of the earmuffs 91B only having the ring 6 (a solid line). FIG. 10 is a graph showing the frequency characteristic R0 (the short dashed line) and a frequency characteristic R12 of the earmuffs 91 having both the rib 31b and the ring 6 (a solid line).

As illustrated in FIG. 8, in a sound range of substantially 400 Hz or less, a sound pressure of the frequency characteristic R1 of the earmuffs 91A only having the rib 31b is smaller than a sound pressure of the frequency characteristic R0, and it is understood that a favorable sound isolation performance is exerted.

As illustrated in FIG. 9, in a sound range of substantially 2000 Hz or les, a sound pressure of the frequency characteristic R2 of the earmuffs 91B only having the ring 6 is smaller than the sound pressure of the frequency characteristic R0, and it is understood that a favorable sound isolation performance is exerted. From these results, in a case where earmuffs with a sound isolation performance of a so called middle-low sound range of 400 Hz or less are necessary, the earmuffs 91A mounted with the rib 31b can be used. Further, in a case where earmuffs with a sound isolation performance of the middle-low sound range including a high sound range close to a middle sound range of 2000 Hz or less is necessary, the earmuffs 91B mounted with the ring 6 can be used. In this manner, depending of use applications of earmuffs, the earmuffs can be divided into models.

Further, the frequency characteristic R2 has a larger degree of reduction in the sound pressure relative to the frequency characteristic R0 than the frequency characteristic R1. Therefore, although the number of components and a cost increase by mounting the ring 6 to earmuffs, earmuffs with a further higher sound isolation effect can be provided.

As illustrated in FIG. 10, in a sound range of substantially 2000 Hz or less, a sound pressure of the frequency characteristic R12 of the earmuffs 91 mounted with both the ring 6 and the rib 31b is remarkably lower than the sound pressure of the frequency characteristic R0, and it is understood that a favorable sound isolation performance is exerted. The reduction amount of the sound pressure of the frequency characteristic R12 relative to the sound pressure of the frequency characteristic R0 is larger than an amount obtained by simply adding the reduction amount of the frequency characteristic R1 and the reduction amount of the frequency characteristic R2, and therefore, the sound isolation performance of the earmuffs 91 is exerted as a synergetic effect of the ring 6 and the rib 31b.

It is understood from the graphs of FIG. 8 to FIG. 10 that a favorable sound isolation performance was exerted for the earmuffs 91A and 91B that have either one of the ring 6 and the rib 31b. Further, it is understood that a sound isolation performance is exerted more highly for the earmuffs 91 having both of the ring 6 and the rib 31b.

The examples that have been described above in detail are not limited to the configurations described above, and modified examples modified within a scope not departing from a scope of the present invention may be adopted.

A type of the headband 912 is not limited to a type of being stretched over a top of a head, but a type of being stretched over on a front side or a back side of a neck may be adopted. For the pad 32, a so called over-the-ear type that completely covers an auricle and is in contact with a side of a head is preferable, but an on-the-ear type to be placed on an auricle is also adoptable. The peripheral groove portion 25 does not need to be continuously formed over an entire circumference. That is, the peripheral groove portion 25 includes groove portions that are interruptedly formed over an entire circumference.

What is claimed is:

1. An earmuff comprising:
a bowl-shaped housing base that includes a first engagement portion on one side thereof;
an annular plate-shaped base plate that includes a second engagement portion and a third engagement portion respectively on a first surface and a second surface on a side opposite to the first surface, and is integrated with the housing base by causing the second engagement portion to be engaged with the first engagement portion; and
a pad portion that includes a pad fixed on the one side and a pad base including a fourth engagement portion on the other side opposite to the one side, and is integrated with the base plate by causing the fourth engagement portion to be engaged with the third engagement portion,
wherein the base plate includes a groove portion adjacent to the third engagement portion and formed at a different position from the third engagement portion, and the pad base includes a rib that enters the groove portion, and
wherein the rib enters the groove portion and restricts an inclination of the third engagement portion involved with an engagement with the fourth engagement portion in a state where the pad base is integrated with the base plate by causing the fourth engagement portion to be engaged with the third engagement portion.

2. The earmuff according to claim 1, wherein
an inner surface of the groove portion is an outer surface of the third engagement portion.

3. The earmuff according to claim 1, wherein
the base plate is formed of a resin and the groove portion is a lightening portion of the second engagement portion.

4. The earmuff according to claim 1, wherein
a ring that is elastic in a compression direction is provided between the housing base and the base plate, and the first engagement portion compresses the ring in a state where the second engagement portion is caused to be engaged with the first engagement portion.

5. The earmuff according to claim 4, wherein
the ring is arranged on a side opposite to the third engagement portion across the groove portion.

* * * * *